United States Patent [19]

Stitt

[11] Patent Number: 5,069,903
[45] Date of Patent: Dec. 3, 1991

[54] THERAPEUTIC AND NUTRITIVE FLAX SEED COMPOSITION AND METHODS EMPLOYING THE SAME

[76] Inventor: Paul A. Stitt, 123 Cleveland Ave., Manitowoc, Wis. 54220

[21] Appl. No.: 629,036

[22] Filed: Dec. 19, 1990

Related U.S. Application Data

[63] Continuation of Ser. No. 133,967, Dec. 16, 1987, abandoned.

[51] Int. Cl.$^5$ .................... A61K 35/78; A61K 33/32
[52] U.S. Cl. ................... 424/195.1; 424/641; 514/552; 514/558; 426/623; 426/629; 426/630
[58] Field of Search ............ 424/195.1, 641; 514/552, 558; 426/623, 629, 630

[56] References Cited

U.S. PATENT DOCUMENTS

| | | | |
|---|---|---|---|
| 59,255 | 10/1866 | Otis | 47/19 |
| 949,416 | 2/1910 | Davis | 426/63 |
| 1,627,921 | 3/1927 | Miner | 426/630 |
| 3,246,989 | 4/1966 | Baehl | 426/18 |
| 4,543,264 | 9/1985 | Stahel | 426/629 |
| 4,918,104 | 4/1990 | Weiss et al. | 514/560 |

OTHER PUBLICATIONS

Franklin, The Aust. Vet. J., Dec. 1944, pp. 332–337.
The Vet. J. 80:33–34, 1924.
Circle or Family Cicle Magazine.
Ensminger, Food For Health, Pegus Press, 1986.
Schlamb, Kermit F., C. O. Clagett and Reece L. Bryant, "Comparison of the Chick Growth Inhibition of Unheated Linseed Hull and Cotyledon Fractions," Poultry Science, vol. XXXIV, No. 6, Nov., 1955.
Klosterman, H. J., G. L. Lamoureux and J. L. Parsons, "The Chemistry of the Flaxseed Antipyridoxine Factor," presented at the meeting of the Flax Institute of the U.S.A., 1965.
Glob, P. V., "Like-Like Man Preserved 2,000 Years in Peat", the National Geographic Magazine, p. 419 (Mar. 1984).
Glob, P. V., "The Bog People, Iron-Age Man Preserved", Cornell University Press, Ithaca, New York, pp. 33, 133 and 180 (date missing).
Hartling, C. "Lein und Leinsamen, eine uralte Kulturpflanze, eine zu Unrecht umstrittene Droge", *Deutsche Apotheker-Zeitung*, 109:27; 1025–1028 (Jul. 3, 1969) and translation.
Brummer, J. N., "Leinsamen—seine Qualitatsmerkmale and ein moglicher Gehalt an Blausaure im Brot" *Brot und Geback*, 9:170–174 (1969) and translation thereof.

*Primary Examiner*—John W. Rollins
*Attorney, Agent, or Firm*—Sughrue, Mion, Zinn, Macpeak & Seas

[57] ABSTRACT

A stable dry edible flax seed composition comprising ground raw flax seed. An animal feed blend comprising: (1) animal feed, and (2) the above-described flax seed composition. A method for improving the general health and appearance of animals, increasing Omega-3 content of animal tissue and decreasing the cholesterol content of animal tissue comprising administering orally to a subject a biologically effective amount of the above-described flax seed composition. A method for improving the general health and appearance of human beings and Omega-3 content of human being tissue comprising administering orally to a human being a biologically effective amount of the above-described flax seed composition. A method for producing the above-described stable dry edible flax seed composition comprising grinding raw flax seed at a temperature of from about 160° F. to just above freezing. The flax seed composition can additionally comprise zinc and/or vitamin B-6.

54 Claims, No Drawings

THERAPEUTIC AND NUTRITIVE FLAX SEED COMPOSITION AND METHODS EMPLOYING THE SAME

This is a continuation of application Ser. No. 07/133,967, filed Dec. 16, 1987, now abandoned.

FIELD OF THE INVENTION

The present invention relates to a therapeutic and nutritive flax seed composition useful to improve human and animal health, to increase the Omega-3 content of human and animal tissue to decrease the cholesterol content of body tissue. More particularly, the present invention relates to a stable dry edible flax seed composition and an animal feed blend comprising the flax seed composition. The present invention also relates to a method for improving the general health and appearance of animals, increasing the Omega-3 content of animal tissue and decreasing the cholesterol content of animal tissue, which includes improving the strength of animal bones, improving the general health of animal offspring, improving the strength of hooves, increasing the growth rate of animals, improving the silkiness and sheen of animal fur and hide, increasing the strength of egg shells of avians, increasing the egg production of avians, increasing the Omega-3 content in edible animal products, and decreasing the cholesterol content of avian eggs. The present invention further relates to a method for improving the general health and appearance of human beings and increasing the Omega-3 content of human tissue which includes improving bone strength, improving the sheen of hair and/or skin, lowering blood pressure, and increasing the Omega-3 content of nursing mothers milk. The present invention additionally relates to a method of producing the stable dry edible flax seed composition.

BACKGROUND OF THE INVENTION

Numerous attempts have been made to improve the general health and appearance of humans and animals, including improving the bone strength of humans and animals and the silkiness of the sheen of animal fur and hides and of human hair and skin. Attempts have also been made to increase the Omega-3 content of edible animal products. Most attempts at improving bone strength, the silkiness and the sheen of hair, fur, skin and hide, and of increasing the Omega-3 content of edible animal products have not been entirely successful and in some cases undesirable side effects have resulted.

Poor animal health is one of the main problems of animal raisers and poor health amongst humans has resulted in a 450 billion dollar human disease business in 1986.

Weak, brittle bones have been attributed to a lack of calcium in the diet. However in broiler chickens even when calcium levels are optimized, approximately one out of ten broilers has a broken leg at the time of slaughter. In humans, it has been reported by D. M. Hegsted (*Journal of Nutrition* 116:2318-2319 (1986)) that in areas of the world where calcium consumption is highest, there are also high levels of osteoporosis and hip fractures. Clearly calcium alone will not solve the problem of weak bones. Accordingly, other factors need to be studied that might be important in making strong bones.

Further few studies have looked at Omega-3 deficiency as a possible cause of general poor health such as weak bones, dull hair, and high blood pressure, although Omega-3 deficiency has been linked to cardiovascular problems and is believed to lower the incidence of cancer, diabetes, arthritis, and other degenerative diseases ("Omega-3 Phenomenon" by Donald Rudin, M.D. (1987) Rawson Assoc. N.Y.).

While flax seed is known to contain Omega-3, as linolenic acid, no reports are known to the present inventor of attempts to use flax seed as a source for the Omega-3 to try to improve human or animal health or to try to increase the Omega-3 content of edible animal products. This is probably because the prevailing view in the art has been that raw whole flax seed contains toxins harmful to humans as well as animals.

For example, it has been reported that flax seed inhibits growth and is harmful to chickens, and by inference, to humans (Schlamb, K. F., *Poultry Science*, p. 1404 (1955)). Another study reported that flax seed contains a factor called antipyridoxine factor that is toxic to poultry (Klosterman. H. J. in a study presented at the Flax Institute of the U.S.A. in 1965).

Similarly, U.S. Pat. No. 4,543,264 discloses in one example that raw flax seed killed all of the turkey polts to which it was fed. Thus the teaching is that raw flax seed must be extracted with alcohol and heated, which removes the Omega-3 containing oil from the flax seed, before flax seed can be consumed.

Further, in the book "Food For Health" (Ensminger and Rolson (1986)) it is stated that flax seed contains a toxic glucoside which must be detoxicated by heating before eating.

Where flax seed has been proposed for use in animal feed, the flax seed is processed first in order to remove the Omega-3-containing oil.

For example, U.S. Pat. No. 4,543,264, referred to above, discloses feeding processed flax seed-containing feed to cows and turkey polts. The flax seed is processed by an alcohol method which removes the Omega-3-containing oil from the flax seed. Further, the control used in the turkey poult study involves feeding non-processed flax seed to the turkey poults. All of the turkey poults fed non-processed flax seed died before the trials ended.

U.S. Pat. No. 3,246,989 discloses a fermented feed for calves. The fermented feed contains 20-30% linseed meal or extracted course-ground linseed. Both linseed meal and extracted course-ground linseed, by definition, have had the Omega-3-containing oil removed therefrom.

Similarly, U.S. Pat. No. 59,255 discloses animal feed containing a small amount of oil or flax seed meal. As mentioned above, flax seed meal is flax seed that has been treated to remove as much Omega-3-containing oil as possible.

U.S. Pat. No. 949,416 discloses cattle food consisting of 84% old processed oil meal. The patent defines "old processed oil meal" as meal that is made from flax seed by grinding or pressing the oil from the seed, instead of extracting the oil with acids. Thus, the disclosure is that the flax-seed meal used in the food has had as much Omega-3-containing oil as possible removed.

Additionally, U.S. Pat. No. 1,627,921 discloses animal feed containing treated roughages. One of the roughages can be flax plant by-product Since flax seed is a main product of the flax plant, the disclosure is that flax seed would not be expected to be part of the roughage.

More recently, it has been shown that flax seed contains from 0.1 to 0.8% cyanogenic glycosides (Schilcher, H. and Wilkens-Sauter, *Zietschr. Fette-Seif-*

*en-Anstrichmittel*, pp. 113–117, Aug. 1986). It has also been reported that this glycoside (linamarin) can be split to release cyanide only in a weakly sour environment (pH 5.5 to 6), and cannot be split in a strongly sour environment as normally exists in human or animal stomachs (Schilcher, H. Berlin, V. Schulz, Koln, and A. Nissler, Herrenberg, *Zietschrift fur Phytotherapie* 7:113–117 (1986)). Further, no side effects or toxic signs were observed when humans consumed as much as 300 grams per day of whole raw flax seed, although no benefits were reported from consumption of the whole raw flax seed.

Despite this observation, there still exists drawbacks to using flax seed to obtain Omega-3 for consumption, namely the rate at which extracted linolenic acid turns rancid. When linolenic acid is extracted from flax seed to make linseed oil paint, it turns rancid within seconds. Rancid linseed oil is very unpalatable to humans and animals and is also highly toxic to humans and animals.

SUMMARY OF THE INVENTION

Accordingly, one object of the present invention is to provide a stable flax seed composition as a source of Omega-3 in the diet.

A second object of the present invention is to provide an edible source of Omega-3 for animals and humans which is abundant and has a flavor liked by animals and humans.

A third object of the present invention is to provide a source of Omega-3 which costs much less than fish.

A fourth object of the present invention is to provide an animal feed containing raw flax seed which is not toxic to the animals.

A fifth object of the present invention is to provide a method for improving the general health and appearance of animals, increasing the Omega-3 content of animal tissue and decreasing the cholesterol content of animal tissue, which includes improving the bone strength of animals which does not depend on calcium consumption alone, improving the general health of animal offspring, improving the strength of hooves of hooved animals, increasing the growth rate of animals, improving the silkiness and the sheen of animal fur and hides by economical and natural means, improving egg shell strength of avians which does not depend on calcium or vitamin D consumption, increasing the egg production of avians, increasing the Omega-3 content of edible animal products such as meat and eggs so that these products can themselves be further sources of Omega-3 in the diet, and decreasing the cholesterol content of avian eggs.

A sixth object of the present invention is to provide a method for improving the general health and appearance of human beings and increasing the Omega-3 content of human tissue, including improving bone strength which does not depend on calcium consumption alone, lowering blood pressure, and increasing the Omega-3 content of nursing mother's milk.

These and other objects have been attained by providing a stable dry edible flax seed composition comprising ground raw flax seed. In a preferred embodiment, the composition further comprises zinc and/or vitamin B-6.

The present invention also provides an animal feed blend comprising: (1) animal feed, and (2) the above-described flax seed composition.

In a further embodiment, the present invention provides a method for improving the general health and appearance of animals, increasing Omega-3 content of animal tissue and decreasing the cholesterol content of animal tissue comprising administering orally to a subject a biologically effective amount of the above-described flax seed composition.

In a still further embodiment, the present invention provides a method for improving the general health and appearance of human beings and increasing Omega-3 content of human being tissue comprising administering orally to a human being a biologically effective amount of the above-described flax seed composition.

The present invention also provides a method for producing the above-described flax seed composition comprising grinding raw flax seed at a temperature of from about 160° F. to just above freezing. In a preferred embodiment, this method further comprises compounding the ground raw flax seed with zinc and/or vitamin B-6.

DETAILED DESCRIPTION OF THE INVENTION

As used herein, the term "Omega-3" refers to three compounds: alpha linolenic acid (LNA), and its biologically active metabolic products found only in animal products, docosohexenoic acid (DHA) and eicosopentenoic acid (EPA).

Also, as used herein, the phrases "animal tissue" and "human tissue" include body tissue as well as body fluids.

The stable dry edible flax seed composition according to the present invention comprises ground raw flax seed. The flax seed is ground to a size of from about 1/10 inch to about 1/1000 inch in diameter. A diameter of about 1/50 to about 1/100 inch is especially preferred.

Grinding is necessary so that Omega-3 present in the seed is made available to the body in the digestive system.

The composition is then administered orally, either by itself or mixed with suitable animal feed or human food.

In a preferred embodiment, the ground flax seed is fortified with zinc and/or Vitamin B-6.

The zinc can be in any form in which it is made available to the digestive tract. For example, the zinc can be in the form of zinc sulfate, zinc oxide or edible mixtures containing zinc.

The vitamin B-6 can also be in any form in which it is made available to the digestive tract. Suitable forms of vitamin B-6 include, pure vitamin B-6, edible mixtures containing vitamin B-6, and vitamin B-6 enriched yeast.

The amount of zinc (expressed as pure zinc) in the flax seed composition ranges from about 1 to about 500 ppm, preferably from about 25 to about 250 ppm, and especially preferably from about 50 to about 200 ppm.

The amount of vitamin B-6 in the flax-seed composition ranges from about 1 ppm to about 250 ppm, preferably from about 5 to about 150 ppm, and especially preferably from about 10 to about 100 ppm.

In studies on animals no acute problems associated with the cyanide found in the cyanogenic glycoside have been observed, whether the flax was consumed in the raw ground state and fortified with vitamin B-6 and zinc or not. However, a slower growth rate has been observed whenever the flax seed or the total diet is not fortified with vitamin B-6 and/or zinc. Further, in U.S. Pat. No. 4,857,327, I disclose that research with humans indicated fortification with vitamin B-6 and zinc was important to prevent chronic illnesses such as acrodemia.

In order to grind the flax seed, any method can be used as long as the proper size ground flax seed is produced and as long as the temperature is maintained at about 160° F. to just above freezing in order to prevent oxidation of the linolenic acid.

Suitable methods of grinding the flax seed can readily be determined by those skilled in the art and include the use of grinders such as a hammermill, impact grinder or Alpine grinder (manufactured by Alpine American Corporation, Natick, Mass.).

If the ground flax seed is to be fortified with zinc and/or vitamin B-6, the zinc and/or vitamin B-6 is simply added to the ground flax seed and thoroughly mixed.

The stable dry edible composition of flax seed produced according to the method of the present invention can be kept for six months or longer at room temperature with no signs of rancidity, i.e. the composition is chemically stable. This is entirely unexpected.

Preferred storage conditions are from about −25° C. to about 50° C., more preferably from about −10° C. to about 40° C., most preferably from about −5° C. to 30° C.

The composition also is especially high in available Omega-3 and is such that the Omega-3 is more easily and quickly digested by the animal or human body as compared to Omega-3 in dry compositions containing whole flax seed, i.e. flax seed that has not been ground.

The present invention also provides an animal feed blend comprising: (1) animal feed, and (2) the above-described stable, edible flax seed composition.

The animal feed blend is produced by mixing the above-described stable, dry, edible flax seed composition with conventional animal feed at the rate of from about one part to about 35 parts by weight of flax seed composition to about 100 parts by weight of animal feed. A more preferred range is from about 5 to about 25 parts by weight of the flax seed composition to 100 parts by weight of animal feed. The most preferred range is from about 10 to about 20 parts by weight flax seed composition to about 100 parts by weight of animal feed.

The animal feed blend is fed to the animals in the amounts and at intervals commensurate with their normal feeding habits.

In a preferred embodiment, the animal feed blend contains ground raw flax seed fortified with vitamin B-6 and/or zinc.

The animal feed blend is useful for all types of animals, including carnivors such as cats, dogs and minks, monogastrics such as horses and pigs, avians such as chickens and turkeys, and even fish.

The animals can be fed the flax seed composition from birth to death. Further, many desirable effects of the flax seed composition can be found in offspring by feeding the flax seed composition to the pregnant mother beginning as early as conception. The preferred time is to start feeding as young as possible so that the linolenic acid will be in abundance for the development of nerve, brain, and vitreous humour, where the highest concentrations of linolenic acid and its metabolites are normally found.

The animal feed blend is especially useful for feeding young domestic animals, ruminant or otherwise, which employ monogastric digestion, e.g., calves. The flax seed composition obtained through the process of the present invention when combined with conventional animal feed, e.g., a mixture of grains, dried animal products and other material, and then added to water in proportions readily determined by those skilled in the art of feeding animals when fed to calves, lambs or other young domestic animals provides a significant increase in shininess of the coat and bone development compared with that obtained with conventional milk substitutes.

The animal feed blend is especially useful for feeding young fur-bearing animals such as mink. The flax seed composition obtained by the process of the present invention when combined with conventional mink feed, e.g., a mixture of ground poultry, pork, and beef by-products plus other materials, provides a significant increase in bone development, growth rate, nursing mink milk production and luxuriant coat development as compared with that obtained with regular mink feed.

The animal feed blend is especially useful for feeding young chickens, turkeys, geese and other avians. The flax seed composition obtained through the process of the present invention when combined with conventional poultry feed such as animal and vegetable materials and essential vitamins and minerals, when fed to chickens, turkeys and other birds provides significantly better developed birds, which have increased growth rates, stronger bones, higher Omega-3 content in the meat and other edible products such as eggs and lower cholesterol content in the eggs as compared with that obtained with conventional poultry feeds.

The animal feed blend is especially useful for feeding young domestic horses and mature horses. The flax seed composition obtained through the process of the present invention when combined with conventional horse feed, e.g. a mixture of oats, molasses, vitamins and minerals, when fed to pregnant mares and young colts provides a significant increase in size, growth rate, bone development and shiny coat of the colts and when fed to mature horses eliminates dandruff and makes the horse calmer, the bones stronger and the hooves less likely to split as compared with that obtained with regular, commercial horse feed.

The animal feed blend is especially useful for feeding young fish. The flax seed composition obtained through the process of the present invention combined with conventional feed, e.g., a mixture of animal and vegetable matter, provides a significant increase in the Omega-3 content in the muscle tissue, and more disease resistance as compared with that obtained with regular, commercial fish feed.

The animal feed blend is especially useful for feeding young pigs and other young domestic animals. The product obtained through the present invention when combined with conventional feed, e.g., a mixture of animal and vegetable products and vitamins and minerals, when fed to pigs or other young domestic animals provides a significant increase in bone development and a shinier coat, and more Omega-3 in the muscle tissue as compared with that obtained with commercial feed for these animals.

The animal feed is especially useful for feeding laying hens to improve the strength of the shell of the eggs and to increase egg production when combined with conventional feed, e.g. a mixture of animal and vegetable products and vitamins and minerals.

As already mentioned, the amount of animal feed blend fed to the animals in order to obtain the above-described benefits therefrom is the same as that fed to the animals conventionally. Further, the number of daily feedings is the same as the conventional number of daily feedings.

The present invention also provides a method for improving the general health and appearance of animals and increasing Omega-3 content of animal tissue comprising administering orally to a subject a biologically effective amount of the flax seed composition.

In a preferred embodiment, the bone strength of animals is improved, and in an especially preferred embodiment, the bone strength of chickens and turkeys is improved.

In a second preferred embodiment, the subject is a pregnant animal and the general health of the pregnant animal's progeny is improved.

According to this second preferred embodiment, it is especially preferred if the pregnant animal is a pregnant mare. The progeny have improved bone strength, size and conformation and also an increased growth rate relative to progeny of pregnant mares not administered the flax seed composition of the present invention.

In a third preferred embodiment, the method improves the strength of hooves of hooved animals. The method is especially useful for improving the strength of horse hooves.

In a fourth preferred embodiment, the method increases the growth rate of animals. The method is especially useful for increasing the growth rate of minks and chickens.

In a fifth preferred embodiment the method improves the silkiness and the sheen of animal fur and/or hide.

The method is especially preferable for improving the silkiness and sheen of horse and mink fur and hide.

In a sixth preferred embodiment, the method increases the strength of egg shells of avians.

The method is especially perferable for increasing the egg shell strength of laying hens.

In a seventh preferred embodiment, the method increases the egg production of avians.

The method is especially preferable for increasing the egg production of laying hens.

Further, Omega-3 is believed, but not definitely established, to improve animal health by being converted to prostaglandins that act as hormones to control metabolic functions in all cells. Thus it is believed to be beneficial to optimize the amount of linolenic acid being given an animal. This also benefits humans that consume the edible animal products, because the edible tissues from animals fed the flax seed compositions contains increased levels of linolenic acid and its metabolic products, DHA and EPA.

Accordingly, an eighth preferred embodiment of the method increases the Omega-3 content of edible animal products.

The method is especially preferable for increasing the Omega-3 content of chicken meat, laying hen eggs, turkey meat, fish meat and pork.

A ninth preferred embodiment of the method decreases the cholesterol content of avian eggs.

In all of the embodiments of the method, it is preferred that the flax seed composition be fortified with zinc and/or vitamin B-6.

In the above method for improving the general health and appearance of animals and increasing Omega-3 content of animal tissue and in all of the above-described specific embodiments of the method, the biologically effective amount of the flax seed composition is best expressed in terms of the parts by weight of flax seed composition per 100 parts by weight of animal feed fed to the animals in amounts and at intervals commensurate with their normal feeding habits. When expressed in this manner, the biologically effective amounts are the same for all animals and are those already set forth above, i.e., from about one part to about 35 parts by weight of flax seed composition to about 100 parts by weight of animal feed, more preferably from about 5 to about 25 parts by weight of flax seed composition to about 100 parts by weight of animal feed, and most preferably from about 10 to about 20 parts by weight flax seed composition to about 100 parts by weight of animal feed.

However, by reference to the above, one skilled in the art can readily determine dosages in terms of g flax seed composition per kg of body weight for different animals at different ages.

For example, the following are suitable dosages in terms of g flax seed (g Flax) per kg body weight for chickens, horses and minks.

| FLAX CONSUMPTION LEVEL | | | | | |
|---|---|---|---|---|---|
| Chicken Diet g Flax/kg Body Weight | | | | | |
| | Day Old | 2 weeks | 4 weeks | 8 weeks | Adult Layers |
| Ideal | 100 | 50 | 20 | 10 | 4 |
| Widest Range | 10 to 200 | 10 to 150 | 3 to 100 | 1 to 50 | 0.5 to 20 |
| Preferred Range | 25 to 150 | 20 to 100 | 5 to 50 | 3 to 25 | 1 to 10 |
| Most Preferred | 50 to 100 | 40 to 60 | 10 to 30 | 5 to 15 | 2 to 6 |

| Horse Diet g Flax/kg Body Weight | | | |
|---|---|---|---|
| | Colt | Mature Horses | Pregnant and Nursing Horses |
| Ideal | 1.0 | .3 | .6 |
| Widest Range | .1 to 3 | .05 to 1.5 | .5 to 3 |
| Preferred Range | .2 to 2 | .10 to 1.0 | .1 to 2 |
| Most Preferred | .5 to 1.5 | .20 to 0.5 | .3 to 1.0 |

| Mink Diet g Flax/kg Body Weight | | | |
|---|---|---|---|
| | 0 to 3 Months | 3 to 6 Months | 6 Mos. and Older (Breeding Animals) |
| Ideal | 6.0 | 4.0 | 5.0 |
| Widest Range | 1 to 30 | 0.5 to 25 | 1 to 30 |
| Preferred Range | 2 to 20 | 1 to 15 | 2 to 20 |
| Most Preferred | 3 to 10 | 2 to 8 | 2 to 10 |

The present invention also provides a method for improving the general health and appearance of human beings and increasing Omega-3 content of human being tissue comprising administering orally to a human being a biologically effective amount of the stable dry edible flax seed composition.

When administered to human beings, the flax seed composition of the present invention improves bone strength, the sheen of hair and skin, and lowers blood pressure.

Additionally, the Omega-3 content of the milk of nursing mothers is increased by administering the flax seed composition to the nursing mothers.

In order to achieve these effects, the flax seed composition is consumed in a daily amount of from about 0.01 g to about 2 g per kg of body weight, preferably from about 0.1 to about 0.5 g per kg of body weight, and especially preferably from about 0.2 g to about 0.3 g per kg of body weight.

Further, the flax seed composition can be consumed as is or mixed with various foods.

Preferably, the flax seed composition is fortified with zinc and/or vitamin B-6, especially if such are not otherwise provided in the diet.

EXAMPLES

The invention will now be described by reference to specific examples which are not meant to be limiting.

were weighed and then sacrificed. The control chickens averaged 600 grams in weight. The experimental chickens averaged 540 grams. This difference in weight is not significant.

Samples of thigh, breast and liver were taken from the sacrificed chickens for fatty acid analysis. The results are shown in Table 1 below. Also, the radius bone in the wing was analyzed for breaking strength. The results are shown in Table 2 below.

TABLE 1

| | Thigh Meat[1] | | | Breast Meat | | | Liver | | |
|---|---|---|---|---|---|---|---|---|---|
| | $C18:3\omega3$[2] | $C20:5\omega3$[3] | $C22:6\omega3$[4] | $C18:3\omega3$ | $C20:5\omega3$ | $C22:6\omega3$ | $C18:3\omega3$ | $C20:5\omega3$ | $C22:6\omega3$ |
| Control Fed Chickens | .89 | 0 | 0 | .98 | .38 | 1.00 | .61 | .44 | 1.83 |
| Flax Seed Fed Chickens | 11.35 | .44 | .36 | 8.95 | 1.33 | 1.07 | 4.16 | 3.85 | 4.97 |
| Percentage Increase | 1270% | ∞ | ∞ | 910% | 350% | 7% | 680% | 875% | 271% |
| Average Increase in Total Omega-3 | | 1365% | | | 581% | | | 450% | |

[1]Results are expressed as percent by weight of total fat.
[2]C18:3 3 = alpha linolenic acid.
[3]C20:5 3 = eicosopentenoic acid.
[4]C22:6 3 = docosohexenoic acid.

Unless otherwise indicated, all percents, ratios, etc. are by weight.

EXAMPLE 1

Effect of Flax Seed Enriched Diet on Omega-3 Content of Chicken Meat

The purpose of this Example is to demonstrate the increase in Omega-3 content in chicken meat when chickens are fed an Omega-3 rich diet by including a raw ground flax seed composition in the chicken feed.

Forty one-day old meat-type chickens were randomly assigned to two groups. The experimental group was fed a diet that contained 20 percent fortified flax seed composition. The other group of chickens were fed an isocaloric and isonitrogenous diet made without flax.

The compositions of the control and experimental diets are shown in the table below. Both diets contained 20% protein, 3100 kcal/kg energy, 1.0% calcium, 0.42% available phosphorus, 0.75% methionine plus cysteine and 1.30% lysine.

| Diet Formulation (Weight Percent) | | |
|---|---|---|
| | Control | Experimental |
| Corn | 55.18 | 48.64 |
| Soybean | 34.42 | 26.01 |
| Dicalcium Phosphate | 1.45 | 1.41 |
| Limestone | 1.52 | 1.53 |
| Lard | 5.63 | 0 |
| Wheat Middling | 0 | 0.47 |
| Fortified Flax Seed composition[1] | 0 | 20.00 |
| Methionine and cysteine | 0.75 | 0.75 |
| Lysine | 0.20 | 0.35 |
| Premix Vitamins[2] | 1.00 | 1.00 |
| Salt | 0.50 | 0.50 |

[1]Fortified flax seed composition contained 200 ppm of zinc as zinc sulfate plus 100 ppm vitamin B-6.
[2]Premix vitamins: (MnO, 5 grams; Choline chloride (60%), 107 grams; Niacin (50%), 3.2 grams; Pantothenate (25%), 2.4 grams; Riboflavin (220 mg/g), 1.5 grams; $B_{12}$ (.66 mg/g), 2.0 grams; Vitamin A, 45 grams; Vitamin D, 6.5 grams; Vitamin E, 2 grams; Corn, 825.4 grams.)

The chickens from both groups were housed in battery brooders for 4 weeks under identical environmental conditions. After 4 weeks, the chickens, 4 weeks old, The results shown in Table 1 indicate that feeding a diet that contains 20 percent flax seed (4.4 percent linolenic acid) causes a substantial increase in all three types of Omega-3 fatty acids in thigh meat, breast meat and the liver. The increases averaged 800 percent. There was a 1365 percent increase in the thigh muscle, 581 percent increase in the breast muscle and a 450 percent increase in liver in total Omega-3 content compared to control samples.

TABLE 2

| Bone Breaking Strength | |
|---|---|
| Control | 23.8 pounds |
| Experimental | 29.7 pounds |

The results shown in Table 2 indicate a 24.7% increase in bone strength in the Experimental group.

The bone strength tests were carried out according to the procedure of T. D. Crenshaw as published in the Journal of Animal Science, volume 53, No. 3, 1981, pages 827 to 835.

The fatty acid analysis was carried out according to University of Minnesota Analytical Testing Procedures, described below.

Samples of thigh, breast and liver were taken from the sacrificed chickens for fatty acid analysis. Samples from ten birds from each group were pooled, homogenized, and then frozen until analyzed.

A 1 gram sample of tissue was homogenized with 50 ml of chloroform/methanol (2:1. v/v), filtered and washed with NaCl. The chloroform layer containing the lipid extract was removed and taken to dryness under a gentle stream of nitrogen. A 10 mg sample of total lipid was transesterified with 5% HCl methanol at 85° C. for 1-½ hours to form the fatty acid methyl esters (FAME). The FAME's were extracted with 30–60° C. petroleum ether and then concentrated for gas chromatographic analysis by removing the solvent under nitrogen.

A Packard 428 gas chromatograph equipped with a flame ionization detector was used to separate the FAME's. A 50 m by 0.2 mm fused silica-bonded FFAP (free fatty acid phase of derivatized carbonax nitroterephthalic acid polymer) capillary column was used to separate FAME's from 12:0 to 22:6ω3. The temperature was programmed from 190 to 220° C. at 2° C./minute. The injector temperature was 250° C., and the detector temperature was 270° C. Helium was the carrier gas with a column flow of 1.4 ml/minute and a split ratio of 1:65. Peaks were identified by comparison with authentic FAME standards. Peak areas were calculated by a microprocessor.

EXAMPLE II

Effect of Flax Seed Enriched Diet on Horse Coats

Four large Belgian parade horses had a serious dandruff problem requiring brushing twice per day, but the animals still looked dirty. The horses also had a serious hoof cracking problem. They were fed ½ pound of the ground flax seed composition per day in addition to their regular diet of 5 pounds of oats and 45 pounds of hay. After three weeks, the horses' coats were shiny and needed brushing only once per week to remove excess dandruff. After eight months on this diet, the cracks in the hooves Were gone and the hooves looked more transluscent.

EXAMPLE III

Effect of Flax Seed Enriched Diet on Progeny of Female Horses

A Belgian mare that was six months pregnant was fed a fortified flax seed composition at the rate of ¼ pound per day (100 ppm vitamin B-6 and 50 ppm zinc) plus 8 pounds of oats and 40 pounds of hay per day until she had her colt. The colt that was born was stronger, bigger, better boned and had better conformation than her full blooded brothers and sisters. The filly colt grew faster also. She stood 49½ inches tall at 30 days of age. At the same age her full blooded sister was 44½ inches tall. At three months of age the flax-fed colt's hair was 1¼ inches long, very soft and silky like a mink. At the same age, her sister's hair was ¾ inches long, dry and brittle, like a horse.

EXAMPLE IV

Effect of Flax Seed Enriched Diet on Mink

One pen of young mink was fed a control diet and a second pen of young mink was fed an experimental diet comprised of 10 percent fortified flax seed composition. Both diets were identical except for the flax seed composition. The diets consisted of 90 percent animal by-products and 10 percent cereal with or without the fortified flax seed composition. The mink fed flax seed grew faster than the ones fed a regular diet, they ate less, and their coats were noticeably shinier. In just forty days, the animal's fur was thick, soft and silky and ready for harvest (pelting) whereas the animals fed the control diet needed to be fed for eighty days to be ready for pelting.

EXAMPLE V

Effect of Flax Seed Enriched Diet on Egg Shell Strength, Egg Production and Omega-3 Content of Eggs Two groups of 35 laying hens each were fed either an experimental diet or a control diet. Both diets contained 15.5% protein, 2900 Kcal/kg metabolizable energy, 3.5% calcium, 0.50 available phosphorous, 0.55% methionine-cystine and 0.82% lysine by weight. The fortified flax seed composition contained 200 ppm zinc as zinc sulfate and 100 ppm vitamin B-6.

| Diet Formula (Weight Percent) | | |
|---|---|---|
| | Control | Experimental |
| Corn | 62.23 | 46.79 |
| Soybean | 22.78 | 13.16 |
| Dicalcium Phosphate | 2.01 | 1.93 |
| Limestone | 7.88 | 7.88 |
| Lard | 3.57 | 0 |
| Wheat Middlings | 0 | 8.70 |
| Fortified Flax Seed Composition | 0 | 20.00 |
| Methionine | 0.03 | 0.02 |
| Premix vitamins* | 1.00 | 1.00 |
| Salt | 0.50 | 0.50 |

*Premix vitamins: (MnO, 5 grams; Choline chloride (60%), 107 grams; Niacin (50%), 3.2 grams; Pantothenate (25%), 2.4 grams; Riboflavin (220 mg/g), 1.5 grams; $B_{12}$ (.66 mg/g), 2.0 grams; Vitamin A, 45 grams; Vitamin D, 6.5 grams; Vitamin E, 2 grams; Corn, 825.4 grams.)

In order to determine the egg shell strength, the distance the egg shell deformed when a 500 g weight was added was measured according to the procedure described by C. Tyler in *British Journal of Poultry Science*, Volume 2, pages 3 to 16 (1960). The eggs from hens fed the experimental diet deformed 13.0 mm. The eggs from hens fed the control diet deformed 16.4 mm.

This demonstrates that the eggs from the flax seed composition fed hens were 26% stronger.

The egg production at six weeks of age was also determined. The results showed that 98% of the hens fed the fortified flax seed composition layed every day. In contrast, only 85% of the hens fed the control diet layed eggs every day.

Further, the Omega-3 content of the eggs was measured. The results showed that the experimental eggs contained 0.4% Omega-3, while the control eggs only contained 0.1% Omega-3.

The Omega-3 content in the eggs was determined as described in Example 1, except that homogenized egg was used as the sample.

Further, the cholesterol content of the eggs was measured by conventional methods. The results showed that the experimental eggs contained 309 mg. cholesterol, while the control eggs contained 560 mg. cholesterol per egg.

EXAMPLE VI

Effect of Flax Seed Diet on Growth Rate of Chickens

Three groups of chickens were fed either a control or experimental diet with fortified flax seed composition or with non-fortified flax seed composition beginning when they were 1-day old.

| Diet Formulation (Weight Percent) | | | |
|---|---|---|---|
| | | Experimental | |
| | Control | Fortified | Non-Fortified |
| Corn | 59.1 | 26.4 | 26.4 |
| Soy Meal | 35.9 | 15.6 | 15.6 |
| Alfalfa | 0 | 1.5 | 1.5 |
| Field Peas | 0 | 20 | 20 |
| Dicalcium Phosphate | 1.57 | 1.04 | 1.04 |
| Limestone | 1.18 | 1.39 | 1.39 |
| Lard | 1.39 | 0 | 0 |
| Yeast | 0 | 3 | 3 |
| Oats | 0 | 10 | 10 |
| Flax | 0 | 20 | 20 |
| D-L Methionine | 0.28 | 0.48 | 0.48 |

-continued

| Diet Formulation (Weight Percent) | | | |
|---|---|---|---|
| | | Experimental | |
| | Control | Fortified | Non-Fortified |
| Lysine | .01 | .05 | .05 |
| Vitamin Premix* | 1.0 | 1.0 | 1.0 |
| Salt | .5 | .5 | .5 |
| Vitamin B-6 | 0 | .10 | 0 |
| Zinc | 0 | .20 | 0 |

*Vitamin Premix: (MnO, 5 grams; Choline chloride (60%), 107 grams; Niacin (50%), 3.2 grams; Pantothenate (25%), 2.4 grams; Riboflavin (220 mg/g), 1.5 grams; $B_{12}$ (.66 mg/g), 2.0 grams; Vitamin A, 45 grams; Vitamin D, 6.5 grams; Vitamin E, 2 grams; Corn, 825.4 grams.)

All diets contained 2,900 Kilocalories per kilogram, 21% protein, and 0.9% calcium, 0.45% phosphate, 1.03% methionine and 1.2% of lysine by weight.

The chickens were weighed at days 7, 14 and 21. The results are shown in Table 3.

TABLE 3

| Average Weight of Chickens (Grams) | | | |
|---|---|---|---|
| | 7 days | 14 days | 21 days |
| Control | 130 | 285 | 520 |
| Experimental | | | |
| Fortified Flax | 154 | 363 | 680 |
| Non-Fortified Flax | 110 | 221 | 360 |

The results show an exceptionally fast growth rate for the chickens fed the fortified flax seed composition with a slight excess of methionine in the diet. The growth rate for the fortified flax seed fed chickens was considerably above the normal of 450 to 550 grams in 21 days. The chickens fed the non-fortified flax seed composition, having low levels of zinc and vitamin B-6 which would be naturally present in the whole grains survived but did not grow as fast as the control group.

EXAMPLE VII

Effect of Flax Seed Enriched Diet on Young Turkeys

A group of 10 young turkeys was fed a diet comprised of 10 percent fortified flax seed composition added to a regular grower diet made by Purina from 3 weeks of age to 4 months of age. The turkeys thrived. They definitely did not die. The fortified flax seed contained 200 ppm zinc as zinc sulfate plus 100 ppm vitamin B-6.

EXAMPLE VIII

Effect of Flax Seed Enriched Diet on Nursing Mothers

Eight nursing mothers were fed three tablespoons per day of fortified flax seed composition (ground flax seed fortified with 200 ppm zinc sulfate (as zinc) and 100 ppm vitamin B-6). This was equivalent to a dosage of about 0.1 to about 0.2 g/kg of body weight. Samples of their milk were taken before starting to take the fortified flax seed composition and after 4 weeks. The results are shown in Table 4.

TABLE 4

| Omega-3 Content Of Nursing Mother's Milk | | | | |
|---|---|---|---|---|
| | Omega-3 Content (As percent of total fat) | | | |
| | $18:3\omega3$ | | $22:6\omega3$ | |
| Subject | Initial | Final | Initial | Final |
| 1 | 1.00 | 2.22 | .15 | .18 |
| 2 | 1.17 | 2.65 | .19 | .37 |
| 3 | 1.10 | 1.94 | .10 | .22 |
| 4 | 1.41 | 2.23 | .17 | .21 |
| 5 | 1.20 | 1.28 | .14 | .39 |
| 6 | 1.30 | 1.49 | .10 | .10 |
| 7 | 1.41 | 2.14 | .17 | .21 |
| 8 | .88 | .79 | .15 | .13 |
| Average | 1.18 | 1.84 | .146 | .226 |
| | 56% Increase | | 54% Increase | |

The results indicate a 56% increase in alpha linolenic acid and a 15% increase in docosohexenoic acid.

The fatty acid analysis was carried out according to the University of Minnesota Analytical Testing Procedures as follows.

Milk samples taken from nursing mothers were kept frozen until analysis.

Lipids from 2 ml samples were extracted with 3 volumes of chloroform and methanol (2:1, v/v). The samples were mixed well and centrifuged. The aqueous layer was drawn off and the chloroform layer filtered to remove the protein. The $CHCl_3$ layer was then dried under a gentle stream of nitrogen and redissolved in 100 $\mu l$ of $CHCl_3$.

The lipid extracts were spotted onto a silicic acid thin layer chromatography plate and developed in 80/20/1 (30–60° C.) petroleum ether:diethyl ether: acetic acid. The chromatograms were sprayed with 0.1% 2',7'-dichlorofluorescein solution and illuminated with UV light. The lipid classes appeared as distinct bands and these were scraped into glass tubes with teflon caps. The lipid classes are: phospholipids (PL). free fatty acids (FA). triglycerides (TG) and cholesterol esters (CE). Since milk is essentially all TG. only that fraction was analyzed. The lipids were transesterified with 2 ml of 5% HCl/methanol (w/v) at 85° C. for 1 hour. After esterification, the methyl esters were extracted with petroleum ether (30–60° C.), the samples taken to dryness under nitrogen and redissolved in a minimum of petroleum ether for gas chromatographic analysis as follows.

A Packard 428 gas chromatograph equipped with a flame ionization detector was used to separate the methyl esters. Gas chromatographic analysis was carried out on a 50 m by 0.2 mm fused silica capillary column coated with FFAP. The column was temperature programmed from 120 to 220° C. at 2°/minute with an initial hold of 5 minutes and a final hold of 20 minutes. The carrier gas was helium at a flow of 1.84 ml/minute. The split ratio was 1:57. Identification of fatty acid methyl esters was made by comparison with authentic standards. Peak areas were calculated by the use of a microprocessor.

EXAMPLE IX

Effect of Flax Seed Enriched Diet on Blood Pressure

Four elderly men had high blood pressure even though they had been treated for 10 to 20 years with conventional medical therapy. diet and exercise. Their blood pressures before consuming the fortified flax seed composition were: 190/88; 200/102; 180/88; 195/95.

They consumed 45 grams per day of the flax seed composition fortified with 150 ppm vitamin B-6 and 200 ppm zinc as zinc sulfate. This was equivalent to a dosage of about 0.5 g/kg of body weight. No other changes in the diet, medication, or exercise were allowed.

After consuming the fortified flax seed for six weeks, their respective blood pressures were 152/82; 162/80; 168/84; 156/74. This amounted to a 18%/14% reduction in systolic/diastolic blood pressure.

While the invention has been described in detail and with reference to specific embodiments thereof, it will be apparent to one skilled in the art that various changes and modifications can be made therein without departing from the spirit and scope thereof.

What is claimed is:

1. A method for improving general health and appearance of an animal, increasing Omega-3 content of said animal's tissue or decreasing cholesterol content of said animal's tissue comprising administering orally to said animal a biologically effective amount of a stable dry edible composition comprising ground raw flax seed.

2. The method of claim 1, wherein said composition further comprises zinc, vitamin B-6 or both zinc and vitamin B-6.

3. The method of claim 2, wherein said biologically effective amount is an amount sufficient to increase bone strength of said animal.

4. The method of claim 3, wherein said animal is a chicken.

5. The method of claim 3, wherein said animal is a turkey.

6. The method of claim 2, wherein said animal is a hooved animal and said biologically effective amount is an amount sufficient to improve hoof strength of said animal.

7. The method of claim 6, wherein said animal is a horse.

8. The method of claim 2, wherein the biologically effective amount is an amount sufficient to increase growth rate of said animal.

9. The method of claim 5, wherein said animal is a mink.

10. The method of claim 5, wherein said animal is a chicken.

11. The method of claim 2, wherein the biologically effective amount is an amount sufficient to improve silkiness and sheen of fur, of hide, or of both fur and hide of said animal.

12. The method of claim 11, wherein said animal is a mink.

13. The method of claim 11, wherein said animal is a horse.

14. The method of claim 2, wherein said animal is an avian and the biologically effective amount is an amount sufficient to increase egg shell strength of eggs laid by said avian.

15. The method of claim 14, wherein said animal is a laying hen.

16. The method of claim 2, wherein said animal is an avian and said biologically effective amount is an amount sufficient to increase egg production of said avian.

17. The method of claim 16, wherein said animal is a laying hen.

18. The method of claim 1, wherein said biologically effective amount is an amount sufficient to increase bone strength of said animal.

19. The method of claim 18, wherein said animal is a chicken.

20. The method of claim 18, wherein said animal is a turkey.

21. The method of claim 1, wherein said animal is a hooved animal and said biologically effective amount is an amount sufficient to improve hoof strength of said animal.

22. The method of claim 21, wherein said animal is a horse.

23. The method of claim 1, wherein the biologically effective amount is an amount sufficient to increase the growth rate of said animal.

24. The method of claim 23, wherein said animal is a mink.

25. The method of claim 23, wherein said animal is a chicken.

26. The method of claim 1, wherein the biologically effective amount is an amount sufficient to improve silkiness and sheen of fur, of hide, or of both fur and hide of said animal.

27. The method of claim 25, wherein said animal is a mink.

28. The method of claim 26, wherein said animal is a horse.

29. The method of claim 1, wherein said animal is an avian and the biologically effective amount is an amount sufficient to increase egg shell strength of eggs laid by said avian.

30. The method of claim 29, wherein said animal is a laying hen.

31. The method of claim 1, wherein said animal is an avian and said biologically effective amount is an amount sufficient to increase egg production of said avian.

32. The method of claim 31, wherein said animal is a laying hen.

33. A method for increasing Omega-3 content of an edible product of an animal comprising administering orally to said animal a biologically effective amount of a stable dry composition comprising ground raw flax seed.

34. The method of claim 33, wherein said composition further comprises zinc, vitamin B-6 or both zinc and vitamin B-6.

35. The method of claim 34, wherein said animal is a chicken and said edible product is a chicken meat.

36. The method of claim 34, wherein said animal is a laying hen and said edible product is eggs.

37. The method of claim 34, wherein said animal is a turkey and said edible product is turkey meat.

38. The method of claim 34, wherein said animal is a fish and said edible product is fish meat.

39. The method of claim 33, wherein said animal is a pig and said edible product is pork.

40. The method of claim 33, wherein said animal is a chicken and said edible product is chicken meat.

41. The method of claim 33, wherein said animal is a laying hen and said edible product is eggs.

42. The method of claim 33, wherein said animal is a turkey and said edible product is turkey meat.

43. The method of claim 33, wherein said animal is a fish and said edible product is fish meat.

44. The method of claim 33, wherein said animal is a pig and said edible product is pork.

45. A method for decreasing cholesterol content of an edible product of an avian, comprising administering orally to said avian a biologically effective amount of a stable dry composition comprising ground raw flax seed.

46. The method of claim 45, wherein said composition further comprises zinc, vitamin B-6 or both zinc and vitamin B-6.

47. The method of claim 46, wherein said avian is a laying hen.

48. The method of claim 45, wherein said avian is a laying hen.

49. A method for improving general health and appearance of expected progeny of a pregnant animal, comprising administering orally to said pregnant animal a biologically effective amount of a stable dry composition comprising ground raw flax seed.

50. The method of claim 49, wherein said composition further comprises zinc, vitamin B-6 or both zinc and vitamin B-6.

51. The method of claim 50, wherein said pregnant animal is a pregnant mare and said biologically effective amount is an amount sufficient to improve bone strength, size and conformation of said expected progeny.

52. The method of claim 50, wherein said pregnant animal is a pregnant mare and said biologically effective amount is an amount sufficient to improve the growth rate of the pregnant mare's expected progeny.

53. The method of claim 49, wherein said pregnant animal is a pregnant mare and said biologically effective amount is an amount sufficient to improve bone strength, size and conformation of said expected progeny.

54. The method of claim 49, wherein said pregnant animal is a pregnant mare and said biologically effective amount is an amount sufficient to improve the growth rate of the pregnant mare's expected progeny.

* * * * *